United States Patent [19]

Patil et al.

[11] Patent Number: 4,897,417
[45] Date of Patent: Jan. 30, 1990

[54] PRODRUGS OF 3,4-HYDROXY BENZOYLOXYPROPANOLAMINES

[75] Inventors: Ghanshyam Patil, Vernon Hills, Ill.; William L. Matier, Hockessin, Del.; Khuong H. X. Mai, Chatworth, Calif.

[73] Assignee: E. I. Du Pont de Nemours & Co., Wilmington, Del.

[21] Appl. No.: 285,006

[22] Filed: Dec. 15, 1988

[51] Int. Cl.$^4$ .................... A61K 31/24; C07C 101/48
[52] U.S. Cl. .................... 514/461; 514/237.8; 514/330; 514/374; 514/451; 514/452; 514/428; 514/487; 544/162; 546/237; 548/215; 548/237; 548/538; 549/372; 549/425; 549/487; 560/110
[58] Field of Search .................... 549/487, 425, 372; 514/461, 237.8, 374, 451, 452, 330, 428, 487; 560/110; 544/162; 548/237, 215, 538; 546/237

[56] References Cited

U.S. PATENT DOCUMENTS

| | | | |
|---|---|---|---|
| 4,195,085 | 3/1980 | Stone | 514/236.2 |
| 4,402,974 | 9/1983 | Matier et al. | 560/110 |
| 4,405,642 | 9/1983 | Kam et al. | 560/110 |
| 4,579,867 | 1/1986 | Escobar | 514/544 |
| 4,582,855 | 4/1986 | Kam et al. | 514/478 |
| 4,661,513 | 4/1987 | Berthold | 549/425 |

Primary Examiner—Donald G. Daus

[57] ABSTRACT

In accordance with the present invention, disclosed herein are compounds of the formula

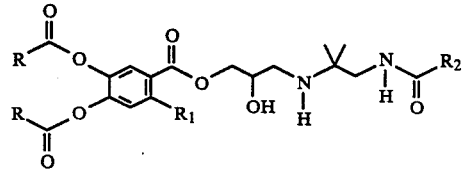

wherein R is straight or branched loweralkyl, $R_1$ is hydrogen, straight or branched loweralkyl, lowercycloalkyl, amino, loweralkoxy or acylamino, and $R_2$ is straight or branched loweralkyl, amino, cyclohexyl, morpholino, piperidino, tetrahydrofuranyl, dihydrofuranyl, tetrahydropyranyl, dioxolanyl, 2,2-dimethyl dioxolanyl, dioxanyl, pyrrolidinyl, tetrahydrooxazolyl, and dihydrooxazolyl, and pharmaceutically acceptable salts thereof. The compounds are useful in the treatment of glaucoma.

24 Claims, No Drawings

PRODRUGS OF 3,4-HYDROXY BENZOYLOXYPROPANOLAMINES

BACKGROUND OF THE INVENTION

Glaucoma is a condition of the eye characterized by increased intraocular pressure. Untreated, the condition can eventually lead to irreversible retinal damage and blindness. Conventional therapy for glaucoma has involved topical administration of pilocarpine and/or epinephrine, and more recently beta-blockers, such as Timolol, administered to the eye several times daily.

Various beta-blocking agents may also be used to lower intraocular pressure. Such use is described, for example, in reviews by W. P. Boger in *Drugs*, 18, 25–32 (1979) and by T. J. Zimmerman and W. P. Boger in *Survey Ophthalmol.* 23(b), 347 (1979). The use of beta-blockers for the treatment of glaucoma is also described in the patent literature. For example, U.S. Pat. No. 4,195,085 to Stone discloses a method for treatment of glucoma by the ocular administration of a beta-blocking compound, timolol maleate. However, these methods also possess significant drawbacks, in that the absorption of the beta-blocking compound into the systemic circulation can cause undesirable life-threatening side effects. Such side effects result from prolonged beta-blocking action on the heart, bronchioles and blood vessels. Accordingly, there is a need for compounds and a method of treatment of glucoma or for lowering intraocular pressure which is relatively free of unwanted systemic side effects.

Certain beta-blocking agents which contain enzymatically labile ester groups are known to exhibit short-acting beta-blocking effects in the systemic circulation. Such short-acting beta-blocking compounds (SAABs) have been suggested for treatment or prophylaxis of cardiac disorders as a means for reducing heart work or improving rhythmicity for a short duration. Such short-acting beta-blocking compounds avoid the sometimes counterproductive effects of conventional beta-blocking agents, whose effects are long-lived and, therefore, difficult to precisely control. Beta-blocking agents having such properties are described in U.S. Pat. Nos. 4,402,974, Sept. 6, 1983; 4,454,154, June 12, 1984; and 4,455,317, June 19, 1984.

SUMMARY OF THE INVENTION

In accordance with the present invention, disclosed herein are compounds of the formula

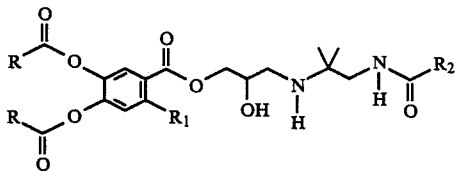

wherein R is straight or branched loweralkyl, $R_1$ is hydrogen, straight or branched loweralkyl, lowercycloalkyl, amino, loweralkoxy or acylamino, and $R_2$ is straight or branched loweralkyl, amino, cyclohexyl, morpholino, piperidino, tetrahydrofuranyl, dihydrofuranyl, tetrahyropyranyl, dioxolanyl, 2,2-dimethyl dioxolanyl, dioxanyl, pyrrolidinyl, tetrahydrooxazolyl, and dihydrooxazolyl, and pharmaceutically acceptable salts thereof. The compounds are useful in the treatment of glaucoma.

DETAILED DESCRIPTION OF THE INVENTION

The compounds of the present invention are ester group containing prodrugs of beta-blockers that have a selective, localized, beta-blocking effect in the eye after topical administration. Such compounds are thought to be very lipophilic prodrugs, which are rapidly metabolized upon entering the systemic circulation and, therefore, will not be available to act as the receptor in the heart and the lungs. It has been discovered that these same compounds are relatively stable in ocular fluids, i.e., lacrimal fluids and aqueous humor, and ocular tissue such as iris-ciliary complex. Consequently, such compounds are useful for the treatment of glaucoma or for lowering intraocular pressure since they remain stable when topically applied to the eye but rapidly metabolize when subsequently absorbed into the systemic circulation. Thus, the method of the present invention provides a very useful therapeutic alternative for the treatment of glaucoma or for lowering intraocular pressure.

The above-mentioned oculoselective beta-blocking compounds will effectively reduce intraocular pressure in the eyes of mammals when topically administered. Because of their short-lived duration of action in the systemic circulation, they will be unavailable to cause severe side effects. Consequently, the present invention resides in the treatment of glaucoma or lowering intraocular pressure with a beta-blocking compound which exhibits relatively long duration of action while in the ocular fluid, but which is subject to relatively rapid breakdown upon passage to the systemic circulation.

Compounds of the present invention are represented by the formula:

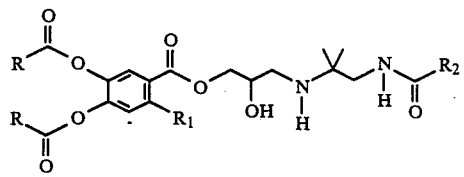

wherein R is straight or branched loweralkyl, $R_1$ is hydrogen, straight or branched loweralkyl, lowercycloalkyl, amino, loweralkoxy or acylamino, and $R_2$ is straight or branched loweralkyl, amino, cyclohexyl, morpholino, piperidino, tetrahydrofuranyl, dihydrofuranyl, tetrahydropyranyl, dioxolanyl, 2,2-dimethyl dioxolanyl, dioxoanyl, pyrrolidinyl, tetrahydrooxazolyl, and dihydrooxazolyl, and pharmaceutically acceptable salts thereof.

Illustrative preferred compounds in accordance with the present invention include, but are not limited to, those in which R is t-butyl, $R_1$ is hydrogen or straight or branched loweralkyl, and $R_2$ is straight or branched loweralkyl, cyclohexyl, morpholino, tetrahydropyranyl or tetrahydrofuranyl.

The term "loweralkyl" as used herein refers to straight or branched chain alkyl radicals containing from 1 to 6 carbon atoms including but not limited to methyl, ethyl, n-propyl, iso-propyl, n-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "lowercycloalkyl" as used herein refers to cyclic saturated aliphatic radicals containing 3 to 6 carbon atoms in the ring, such as cyclopropyl, cyclobutyl, cyclopentyl, or cyclohexyl.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate tartrate, and like salts. Also included are metallic salts such as the sodium or potassium salt of the acid.

The compounds of this invention are advantageously administered topically to the eye in the form of a solution, ointment, or solid insert such as is described in U.S. Pat. No. 4,195,085. Formulations may contain the active compound, preferably in the form of a soluble acid addition salt, in amounts ranging from about 0.01% to about 10% by weight, preferably from about 0.5% to about 5% by weight. Unit dosages of the active compound can range from about 0.001 to about 5.0 mg, preferably from about 0.05 to about 2.0 mg. The dosage administered to a patient will depend upon the patient's needs and the particular compounds employed.

Carriers used in the preparations of the present invention are preferably nontoxic ophthalmologically acceptable pharmaceutical organic or inorganic compositions such as water; mixtures of water and water-miscible solvents, such as lower alcohols; mineral oils; petroleum jellies; ethyl cellulose; polyvinylpyrrolidone and other conventional carriers. In addition, the pharmaceutical preparations may also contain additional components such as emulsifying, preserving, wetting and sterilizing agents. These include polyethylene glycols 200, 300, 400, and 600, carbowaxes 1,000, 1,500, 4,000, 6,000, and 10,000 bacteriocidal components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The method of treatment of this invention advantageously involves the topical administration of eye drops containing the active compound. Formulations for eye drops preferably include the active compound as a soluble acid addition salt in a properly buffered, sterile, aqueous isotonic solution.

The compounds of the present invention are ester group-containing beta-blockers that have a selective, localized, beta-blocking effect in the eye after topical administration. Such compounds are thought to be rapidly metabolized by plasma and/or liver esterases into inactive by-products, upon entering the systemic circulation. It has been discovered that these same compounds are relatively stable in ocular fluids, i.e., lacrimal fluids and aqueous humor. Consequently, such compounds are useful for the treatment of glaucoma or for lowering intraocular pressure since they remain stable when topically applied to the eye but rapidly metabolize when subsequently absorbed into the systemic circulation.

The compounds of the present invention and equivalents thereof possessing substantially similar pharmacological properties may be prepared according to the following reaction schemes, which represent specific embodiments of the invention.

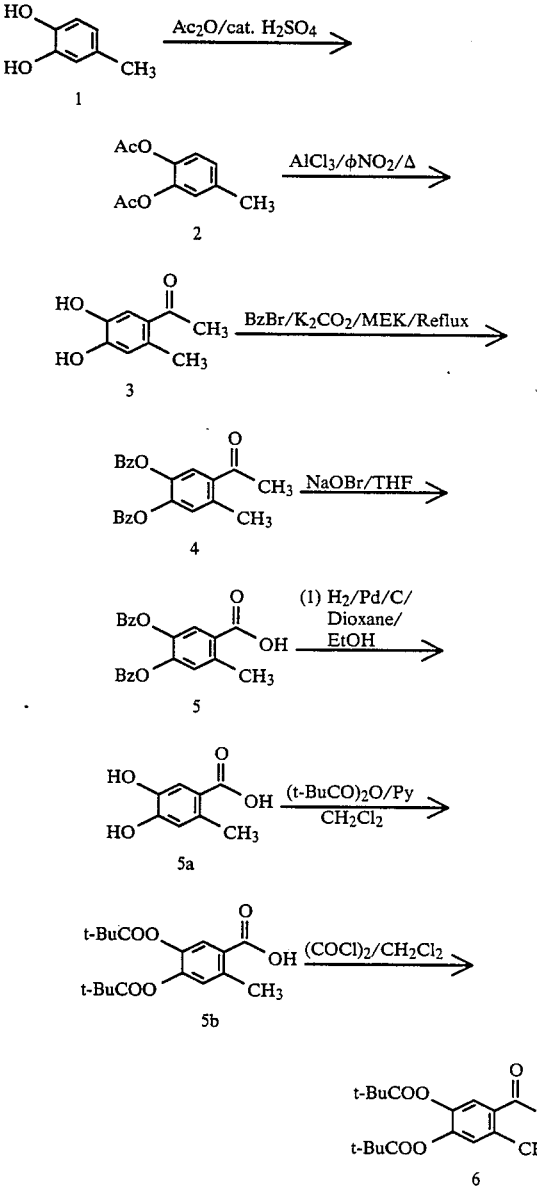

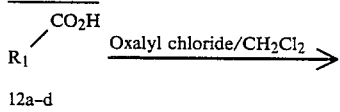

-continued
Synthesis of Compound 8a–d

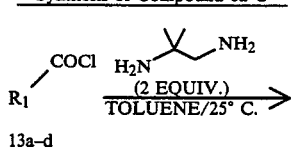
13a–d

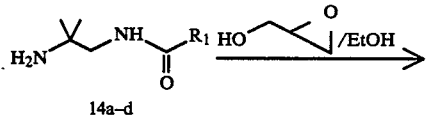
14a–d

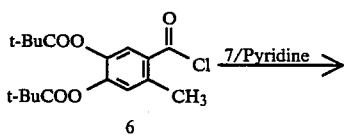
7a–d

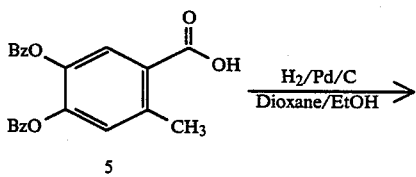
6

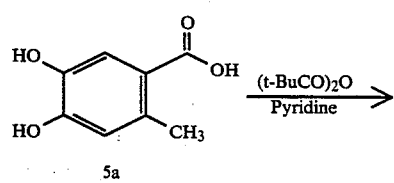
8a–d   OXALATE a = Me
b = i-Pr
c = NH₂
d = 3-Tetrahydrofuranyl or THF

Compound 8d is a prodrug of compound 9d. Since compound 8d is considerably lipophilic, it is expected to penetrate the cornea much more rapidly and effectively.

The following examples are intended to be illustrative of the present invention but should not be considered as limiting the scope thereof.

EXAMPLE 1

A general procedure for the synthesis of compounds 5 to 6 can be presented as follows.

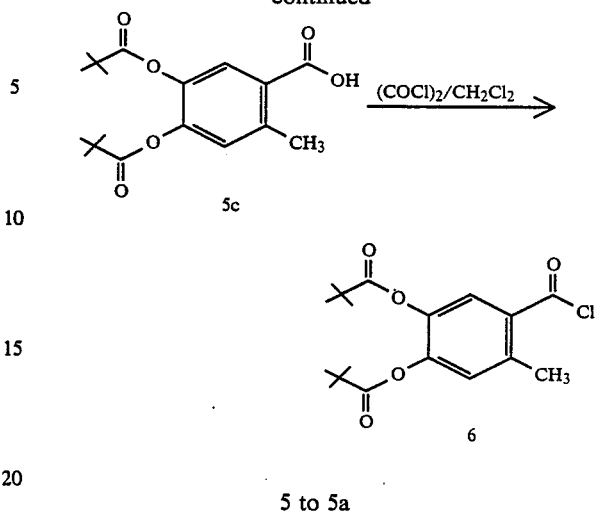

5 to 5a

To a solution of 5 (50 g, 0.14 mole) in a mixture of dioxane and ethanol (200 mL, 1:1) was added 10% Pd/C (0.5 g) and hydrogenated in Parr apparatus for 24 hours. The reaction mixture was filtered over a bed of celite and the filtrate was concentrated in vacuo. The resulting oil was crystallized from cyclohexane to give 24 g (100%) of catechol-acid 5a: m.p. 250° to 252° C. or 250° to 52° C.

5a to 5b

A mixture containing 5a (22 g, 0.13 mole), pyridine (36 g, 0.45 mole) and trimethylacetyl chloride (55 g, 0.45 mole), and ethylenechloride (100 mL) was refluxed for 2 hours. The reaction mixture was evaporated to dryness in vacuo. To this residue was added water (100 mL) and ether (100 mL). After stirring for 5 minutes, the organic layer was separated, washed with 1N HCl (50 mL), followed by brine (50 mL), dried over MgSO₄, and filtered. The filtrate was evaporated in vacuo to give clean, light yellow oil, which was used immediately in the next experiment.

5b to 6

To the residue obtained in the above experiment was added methylenechloride (100 mL) and oxalyl chloride (100 g) and stirred at 22° C. for 3 hours. The reaction mixture was evaporated to dryness in vacuo. The residue was dissolved in 50 mL toluene and evaporated in vacuo to give yellow oil. The traces of toluene were removed under high vacuum to give 50 g (50% g 5a) the acid chloride 6 as an oil. Used as it is in the next experiment.

EXAMPLE 2

A general procedure for the synthesis of compounds 8a to 8d can be represented as follows.

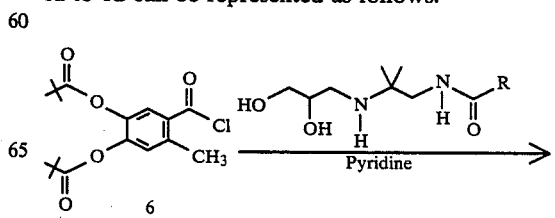

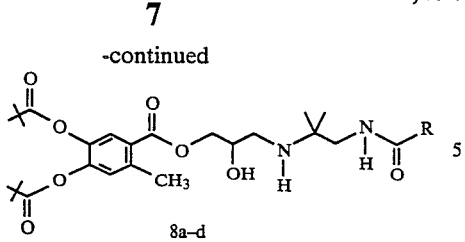

8a-d

To a solution of aminodiol (0.02 mole), pyridine (2 mL) in 30 mL methylenechloride was added a solution of acid chloride 6 (0.02 mole) in methylenechloride (20 mL) and stirred at 22° C. for 15 minutes. The solvent was evaporated in vacuo and to the resulting yellowish residue was added ethylacetate (50 mL), water (50 mL) and potassium carbanate (2 g). The organic layer was separated, washed with brine, dried over MgSO₄, and filtered. The evaporation of solvent in vacuo resulted in yellow residue. This was dissolved in toluene (50 mL) and then evaporated in vacuo. The latter procedure was repeated twice to remove the traces of pyridine. The resulting oil was dissolved in ethylacetate (20 mL) and acidified with a solution of oxalic acid in ethylacetate. If no crystalline solid appeared, then this solution was diluted with ether until cloudy and allowed to stand at 22° C. until the crystalline solid appeared. The product was filtered, washed with ether and air dried. The yields varied from 16 to 40%.

Compounds 12 to 14 can be made in accordance with the following reaction scheme and as described in Examples 3 and 4.

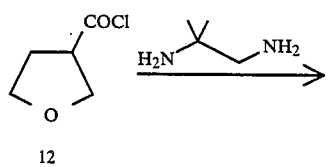

12

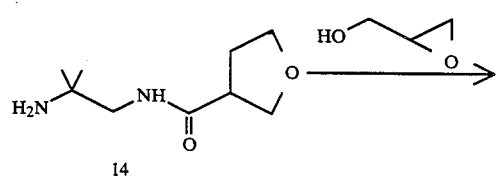

14

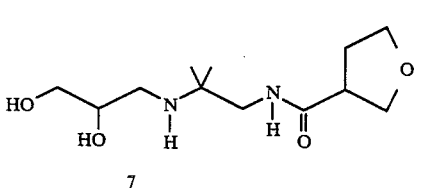

7

EXAMPLE 3

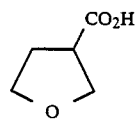

The acid 12 was synthesized by the procedure described in JACS 80, 3905 (1958).

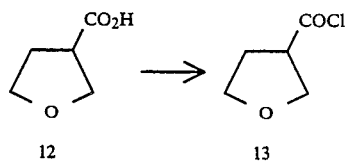

To a solution of acid 12 (29 g, 250 mmoles) in methylene chloride (100 mL), cooled to −5° C., was added oxalyl chloride (39 g, 300 mmoles) under nitrogen over 30 minutes. The cooling bath was removed and the reaction was stirred at room temperature for 1½ hours and then heated under reflux for 3 hours. After solvent removal, the residue was coevaporated with toluene, and then distilled at 77° to 84° C. to give 25 g (74%) of 13.

EXAMPLE 4

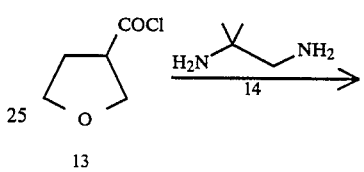

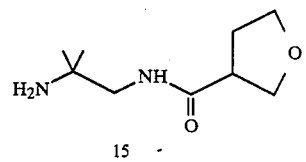

15

To an ice-cooled solution of diamine 14 (7.9 g, 89 mmoles) in toluene (50 mL) was added the acid chloride 13 (6.1 g, 89 mmole) and the mixture was stirred at room temperature for 16 hours. The solution was filtered and the filtrate was evaporated to dryness in vacuo. The residue was coevaporated in vacuo with toluene and acetonitrile, respectively, to give 7.82 g of oil. The oil was redissolved in toluene (50 mL) and the solution was washed with saturated sodium bicarbonate solution, followed by brine, dried (MgSO₄), filtered and evaporated to dryness under high vacuum to give 7.32 g of oil which was used as is in the next experiment.

EXAMPLE 4a

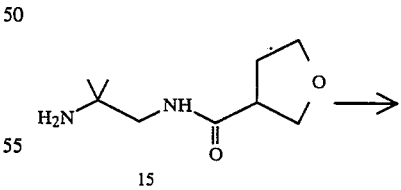

15

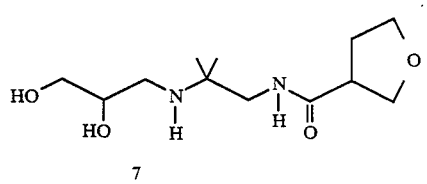

7

The solution of the aminoamide 15 (98.3 g, 0.55 moles) and glycidol (32.6 g, 0.44 moles, freshly distilled) in ethanol (600 mL) was heated under reflux for 1½ hours and then stirred for 16 hours at room temperature. The reaction mixture was evaporated to dryness in vacuo and the residue was coevaporated in vacuo with toluene (3 times) and acetonitrile (once), respectively, to yield 114.5 g (0.44 moles, 80%) of 7 which was used as is in the next step (see Example 5).

EXAMPLE 5

Compound 8d

Ocular Bioavailability in Rabbits (Table 1)

The ocular bioavailability of Timolol and compound 8d (dipivaloyl ester prodrug of compound 9d) was evaluated in New Zealand White Rabbits. Fifty μL of a solution of 0.25% Timolol or 0.5% compound 8d (both in the same vehicle) were administered onto the cornea of both eyes of 48 rabbits (24 rabbits/compound). At 5, 15, 30, 60, 120, 180, 240, and 360 minutes after dosing, 3 rabbits (6 eyes) per compound were killed. Aqueous humor (AH), was quickly removed from the eyes, weighed and processed to determine tissue levels of Timolol or compound 8d and compound 9d.

The results indicate that compound 8d and Timolol were rapidly absorbed in the eye. The area under the AH concentration time curve (AUC$_{0-240'}$) for compound 8d averaged 27,377 and 9,022 ng/100 μL/min for Timolol. Based on the ocular bioavailability results, the AUC of compound 8d in AH after 0.25% is 3× greater than the AUC of Timolol in AH after 0.25% Timolol.

It is concluded that compound 8d effectively delivers compound 9d to the internal structures of the eye and that compound 9d is stable in rabbit ocular tissues.

TABLE 1

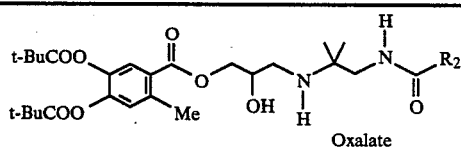

Oxalate

| NO. | R$_2$ | m.p. °C. | Aq. humor AUC |
|---|---|---|---|
| 8a | CH$_3$ | 153–57 | 15,559 |
| 8b | ⤳ | 175–77 | 35,329 |
| 8c | NH$_2$ | 182–84 | — |
| 8d | (tetrahydrofuranyl) | 115–19 | 27,377 |

TABLE 1-continued

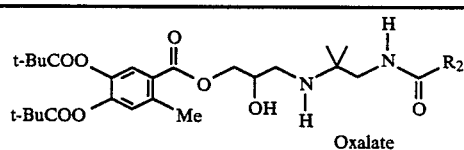

Oxalate

| NO. | R$_2$ | m.p. °C. | Aq. humor AUC |
|---|---|---|---|
| Timolol | | | 9,022 |

EXAMPLE 6

Effect of Compound 8a or 8c on Systemic Beta-Blockade Upon Topical Administration Mongrel dogs were anesthetized and control readings were made at −45 and −30 minutes. Following the −30 minute reading, an infusion of isoproterenol (0.5 μg/kg/min) was begun and maintained during the course of the experiment. Two readings of pretreatment isoproterenol responses were made at 15 minutes and at zero minutes.

At zero minutes, a 50 μL sample of test compound was administered topically. This dose was repeated at 50, 60 and 90 minutes and the animal was monitored for heart rate for 180 minutes following the first application. Heart rate was obtained directly from the strip chart recording.

Compound 8a or 8c upon either single (Table 2) topical applications (50 μL, 0.125% solution) had no effect on the heart rate responses to isoproterenol. Compound 8a or 8c (50 μL at 0.125% solution) demonstrated no systemic beta-blockade of isoproterenol-induced increase in heart rate. By contrast, Timolol (50 μL, 0.125% solution) upon single topical application demonstrated a significant inhibitory effect on the heart rate response to isoproterenol (213–155 bbm).

TABLE 2

The Effects of Topically Administered Compounds 8a and 8c or Timolol on Isoproterenolol-Induced Changes in Heart Rate in Anesthetized Dogs

| Treatment Group | Parameter | −30 | Baseline ISO Only 0 Dose | 15 | 30 | 45 | 60 Dose | Time (min) Post-treatment 90 | 120 Dose | 150 |
|---|---|---|---|---|---|---|---|---|---|---|
| Compound 8a 0.125% | HR (bpm) | 152 | 215 | 214 | 213 | 210 | 208 | 207 | 203 | 202 |
| Compound 8c 0.125% | HR (bpm) | 158 | 212 | 212 | 210 | 210 | 210 | 210 | 210 | 212 |
| Timolol 0.125% | HR (bpm) | 142 | 213 | 198 | 185 | 174 | 174 | 179 | 183 | 192 |
| Vehicle 0.5% (n = 4) | HR (bpm) | 158 | 206 | 205 | 203 | 204 | 204 | 207 | 211 | 216 |

HR = Heart Rate
bpm = beats per minute

SUMMARY

At 0.125% concentration, within 60 minutes, Timolol produced a 39 bpm drop in heart rate whereas at the same concentration, compounds 8a and 8c only produced a 2 bpm and 7 bpm drop, respectively. Note that vehicle also produced a 2 bpm drop in heart rate within 60 minutes.

What is claimed is:
1. A compound of the formula

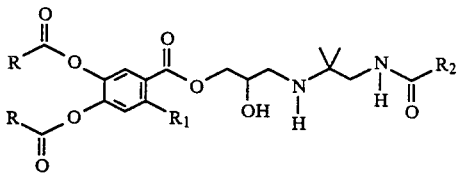

wherein R is straight or branched loweralkyl, $R_1$ is hydrogen, straight or branched loweralkyl, lowercycloalkyl, amino, loweralkoxy or acylamino, and $R_2$ is straight or branched loweralkyl, amino, lowercycloalkyl, morpholino, piperidino, tetrahydrofuranyl, dihydrofuranyl, tetrahydropyranyl, dioxolanyl, 2,2-dimethyl dioxolanyl, dioxanyl, pyrrolidinyl, tetrahydrooxazolyl, and dihydrooxazolyl, or a pharmaceutically acceptable salt thereof.

2. A compound of claim 1 wherein $R_1$ is hydrogen, straight or branched loweralkyl, or loweralkoxy, and $R_2$ is straight or branched loweralkyl, amino, morpholino, piperidino or tetrahydrofuranyl.

3. A compound of claim 2 wherein $R_1$ is straight or branched loweralkyl, and $R_2$ is straight or branched loweralkyl, amino or tetrahydrofuranyl.

4. A compound of claim 3 wherein $R_2$ is methyl, propyl, amino or tetrahydrofuranyl.

5. A compound of claim 1 wherein R is tertiary-butyl, $R_1$ is methyl and $R_2$ is methyl.

6. A compound of claim 1 wherein R is tertiary-butyl, $R_1$ is methyl and $R_2$ is isopropyl.

7. A compound of claim 1 wherein R is tertiary-butyl, $R_1$ is methyl and $R_2$ is amino.

8. A compound of claim 1 wherein R is tertiary-butyl, $R_1$ is methyl and $R_2$ is tetrahydrofuranyl.

9. A method of treating glaucoma or of lowering intraocular pressure in a patient comprising administering to the eye of a patient in need of such treatment a therapeutically effective amount of a compound of the formula

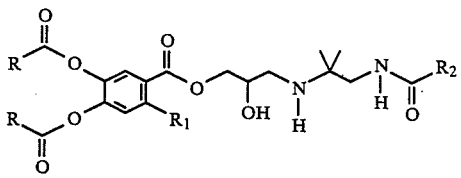

wherein R is straight or branched loweralkyl, $R_1$ is hydrogen, straight or branched loweralkyl, lowercycloalkyl, amino, loweralkoxy or acylamino, and $R_2$ is straight or branched loweralkyl, amino, lowercycloalkyl, morpholino, piperidino, tetrahydrofuranyl, dihydrofuranyl, tetrahydropyranyl, dioxolanyl, 2,2-dimethyl dioxolanyl, dioxanyl, pyrrolidinyl, tetrahydrooxazolyl, and dihydrooxazolyl, or a pharmaceutically acceptable salt thereof.

10. The method of claim 9 wherein $R_1$ is hydrogen, straight or branched loweralkyl, or loweralkoxy, and $R_2$ is straight or branched loweralkyl, amino, morpholino, piperidino or tetrahydrofuranyl.

11. The method of claim 10 wherein $R_1$ is straight or branched loweralkyl, and $R_2$ is straight or branched loweralkyl, amino or tetrahydrofuranyl.

12. The method of claim 11 wherein $R_2$ is methyl, propyl, amino or tetrahydrofuranyl.

13. The method of claim 9 wherein R is tertiary-butyl, $R_1$ is methyl and $R_2$ is methyl.

14. The method of claim 9 wherein R is tertiary-butyl, $R_1$ is methyl and $R_2$ is isopropyl.

15. The method of claim 9 wherein R is tertiary-butyl, $R_1$ is methyl and $R_2$ is amino.

16. The method of claim 9 wherein R is tertiary-butyl, $R_1$ is methyl and $R_2$ is tetrahydrofuranyl.

17. A pharmaceutical composition useful for the treatment of glaucoma or for lowering intraocular pressure, which composition comprises an intraocular lowering effective amount of a compound of the formula

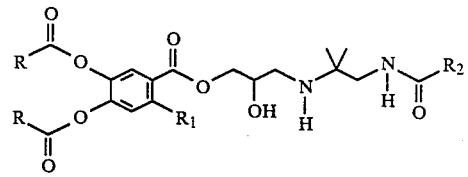

wherein R is straight or branched loweralkyl, $R_1$ is hydrogen, straight or branched loweralkyl, lowercycloalkyl, amino, loweralkoxy or acylamino, and $R_2$ is straight or branched loweralkyl, amino, lowercycloalkyl, morpholino, piperidino, tetrahydrofuranyl, dihydrofuranyl, tetrahydropyranyl, dioxolanyl, 2,2-dimethyl dioxolanyl, dioxanyl, pyrrolidinyl, tetrahydrooxazolyl, and dihydrooxazolyl, or a pharmaceutically acceptable salt thereof.

18. The composition of claim 17 wherein $R_1$ is hydrogen, straight or branched loweralkyl, or loweralkoxy, and $R_2$ is straight or branched loweralkyl, amino, morpholino, piperidino or tetrahydrofuranyl.

19. The composition of claim 18 wherein $R_1$ is straight or branched loweralkyl, and $R_2$ is straight or branched loweralkyl, amino or tetrahydrofuranyl.

20. The composition of claim 19 wherein $R_2$ is methyl, propyl, amino or tetrahydrofuranyl.

21. The composition of claim 17 wherein R is tertiary-butyl, $R_1$ is methyl and $R_2$ is methyl.

22. The composition of claim 17 wherein R is tertiary-butyl, $R_1$ is methyl and $R_2$ is isopropyl.

23. The composition of claim 17 wherein R is tertiary-butyl, $R_1$ is methyl and $R_2$ is amino.

24. The composition of claim 17 wherein R is tertiary-butyl, $R_1$ is methyl and $R_2$ is tetrahydrofuranyl.

* * * * *